(12) United States Patent
Alleyne

(10) Patent No.: US 7,214,226 B2
(45) Date of Patent: May 8, 2007

(54) COMPRESSIBLE FIXATION APPARATUS FOR SPINAL SURGERY

(75) Inventor: Neville Alleyne, La Jolla, CA (US)

(73) Assignee: NAS Spine, Inc., San Diego, CA (US)

( * ) Notice: Subject to any disclaimer, the term of this patent is extended or adjusted under 35 U.S.C. 154(b) by 463 days.

(21) Appl. No.: 10/628,079

(22) Filed: Jul. 24, 2003

(65) Prior Publication Data

US 2004/0097938 A1    May 20, 2004

Related U.S. Application Data

(60) Provisional application No. 60/398,623, filed on Jul. 24, 2002.

(51) Int. Cl.
*A61B 17/56* (2006.01)
*A61B 17/58* (2006.01)

(52) U.S. Cl. .......................................... 606/61; 606/71
(58) Field of Classification Search .................. 606/61, 606/57, 68, 69, 70, 71, 105, 60; 403/340
See application file for complete search history.

(56) References Cited

U.S. PATENT DOCUMENTS

| 2,333,033 | A | * | 10/1943 | Mraz ........................... 606/57 |
|---|---|---|---|---|
| 5,129,903 | A | * | 7/1992 | Luhr et al. ..................... 606/71 |
| 5,180,380 | A |   | 1/1993 | Pursley et al. |
| 5,672,177 | A | * | 9/1997 | Seldin ........................... 606/71 |
| 5,700,263 | A |   | 12/1997 | Schendel |
| 5,902,304 | A | * | 5/1999 | Walker et al. ................ 606/71 |
| 6,126,660 | A |   | 10/2000 | Dietz |
| 6,306,136 | B1 | * | 10/2001 | Baccelli ........................ 606/61 |
| 6,328,738 | B1 |   | 12/2001 | Suddaby |
| 6,355,036 | B1 | * | 3/2002 | Nakajima ..................... 606/57 |
| 6,402,756 | B1 | * | 6/2002 | Ralph et al. .................. 606/71 |
| 6,428,542 | B1 |   | 8/2002 | Michelson |
| 6,533,786 | B1 |   | 3/2003 | Needham et al. |
| 6,576,016 | B1 |   | 6/2003 | Hochshuler et al. |
| 7,029,472 | B1 | * | 4/2006 | Fortin .......................... 606/60 |

FOREIGN PATENT DOCUMENTS

WO    WO 00/72768    * 12/2000

* cited by examiner

*Primary Examiner*—Pedro Philogene
(74) *Attorney, Agent, or Firm*—Knobbe Martens Olson & Bear LLP

(57) ABSTRACT

A spinal fixation apparatus is configured with a pair of endpieces and an intermediate compressible portion. The compressible portion may comprise a pair of mating sliders comprising toothed arms attached to the endpieces. A gear engages the toothed arms. When the gear is rotated, the sliders bring the endpieces together, compressing the apparatus.

14 Claims, 12 Drawing Sheets

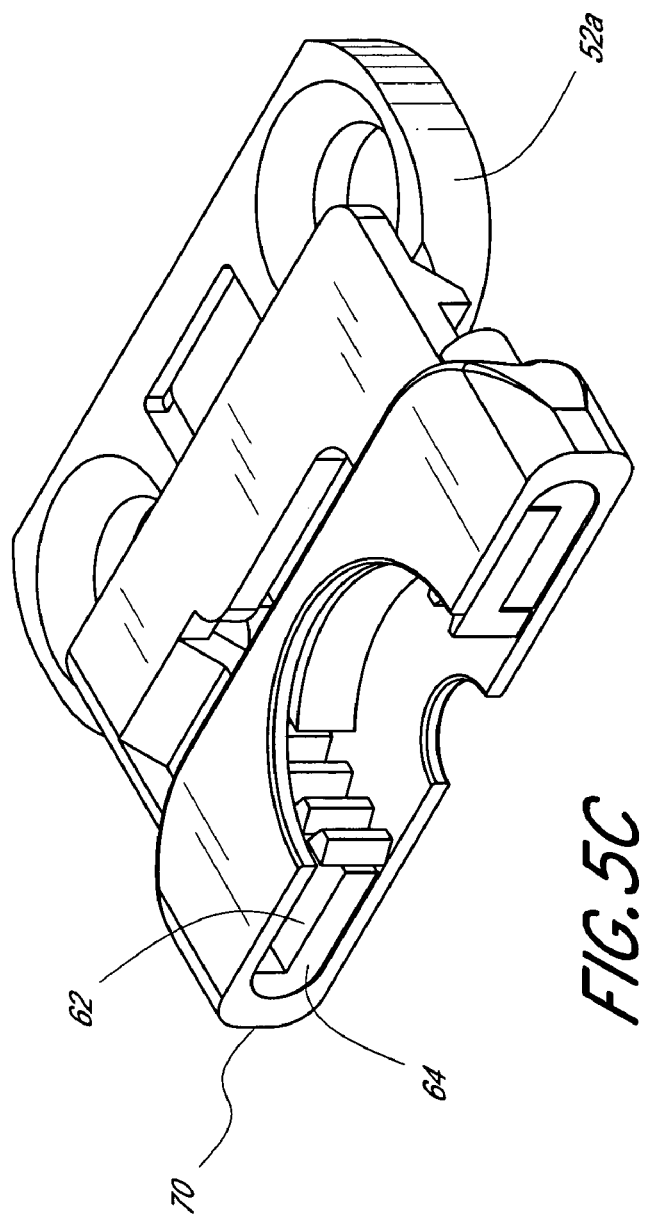

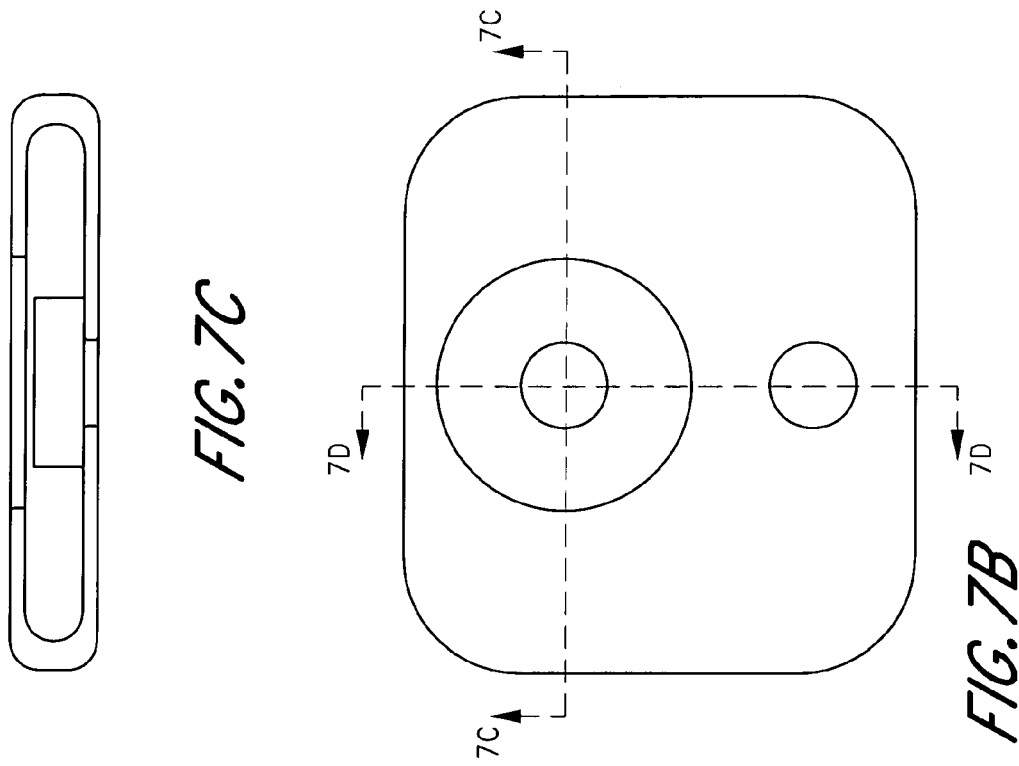
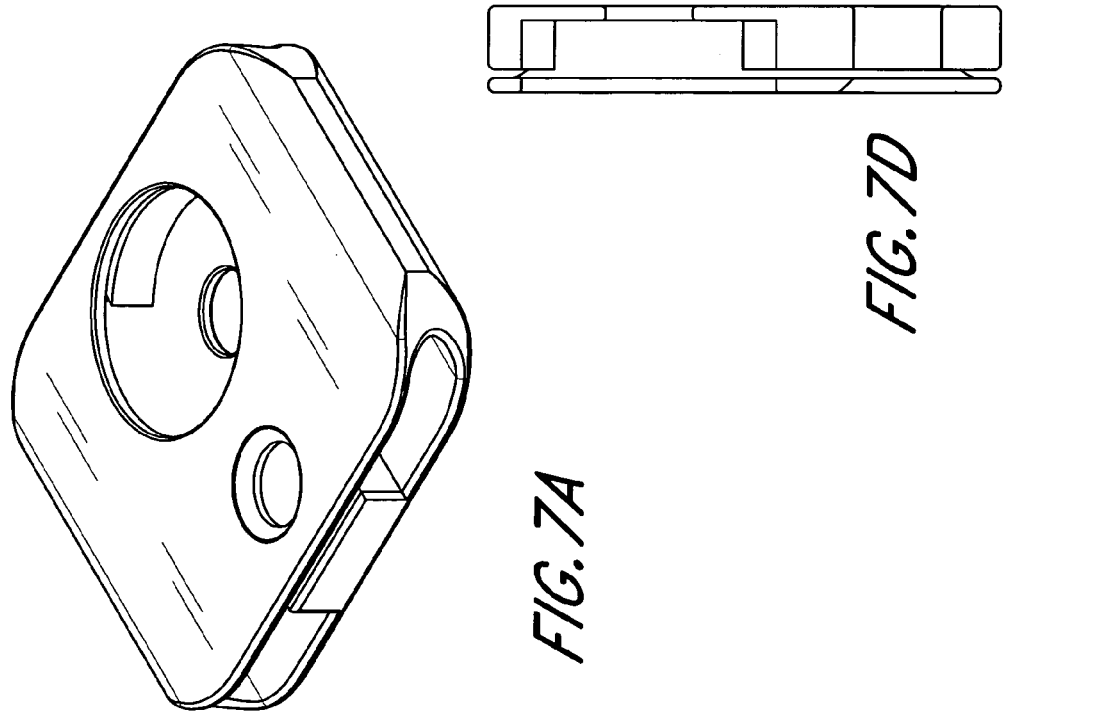

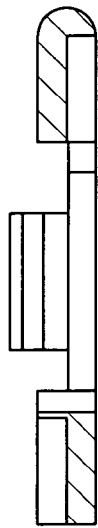
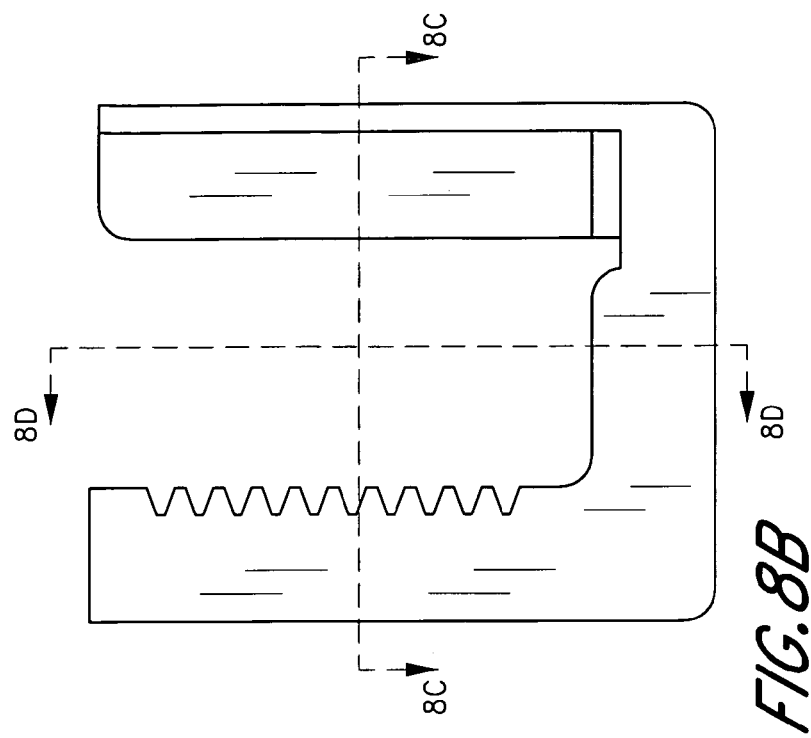
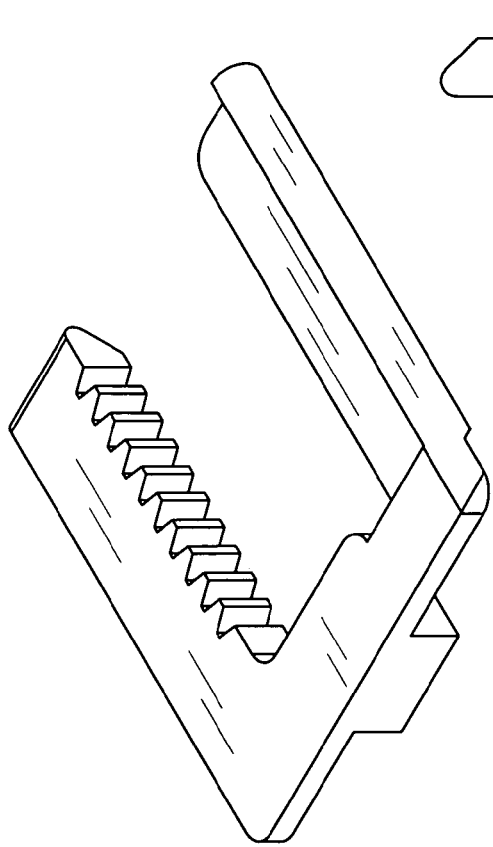
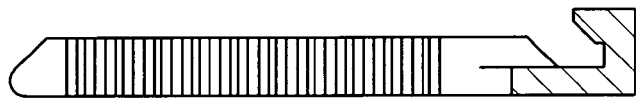

COMPRESSIBLE FIXATION APPARATUS FOR SPINAL SURGERY

CROSS REFERENCE TO RELATED APPLICATIONS

This application claims priority under 35 U.S.C. Section 119(e) to U.S. Provisional Application No. 60/398,623, filed on Jul. 24, 2002.

BACKGROUND OF THE INVENTION

1. Field of the Invention

The present invention relates generally to the field of medical equipment, specifically to a device for use in spinal surgery such as a diskectomy and spinal fusion.

2. Description of the Related Art

Anterior cervical diskectomy and corpectomy have been utilized for the treatment of cervical radiculopathy, myelopathy, and myeloradiculopathy for over 50 years. The traditional methods for treatment of the single level and two-level decompressions have been the Cloward technique and the Smith-Robinson technique. Both techniques typically involve removing the disk and a portion of the end plate and inserting a graft. In the Cloward technique, a circular bone dowel of autologous or allograft bone is inserted into the defect in order to fuse the two adjacent vertebrae. In the Smith-Robinson technique, a horseshoe shaped graft is taken either from the patient's iliac crest or from allograft bone and inserted in the interspace.

The literature over the years shows that such fusions have a relatively poor success rate without stabilization with plate fixation. Some of the reasons for failure include pesudarthrosis, poor fixation (improper placement of the screws), improper placement of the graft, poor fixation of the graft, poor preparation of the cartilaginous end plates, and improper placement of the plate. As fusions, and especially multi-level fusions become more common, the need to improve the fusion rate in these surgeries is becoming more pronounced.

SUMMARY OF THE INVENTION

In one embodiment, the invention comprises an apparatus for the enhancement of fusion of at least two adjacent vertebrae comprising at least a superior and an inferior endpiece, wherein the superior endpiece is adapted to be affixed to a superior vertebral body, and the inferior endpiece is adapted to be affixed to an inferior vertebral body. The apparatus further comprises a compressible portion located between the superior and inferior endpieces. The compressible portion may comprise a sliding mechanism.

In another embodiment, the invention comprises a method of enhancing fusion between vertebral bodies comprising accessing a spinal portion, affixing respective endpieces to superior and inferior vertebral bodies, adjusting the distance between the endpieces into a compressed position, and locking the apparatus in the compressed position.

In another embodiment, the invention comprises a method of manufacturing an apparatus for the enhancement of fusion between at least two adjacent vertebrae comprising attaching a compressible coupling to a superior and an inferior endpiece, wherein the superior and inferior endpieces are adapted to be affixed to a superior and an inferior vertebral body, respectively.

BRIEF DESCRIPTION OF THE DRAWINGS

FIG. 5C is a cross-sectional view of the compressible device of FIG. 1A, taken along line B—B of FIG. 5A.

FIGS. 7A–D illustrate one embodiment of the housing of the device of FIGS. 5A–C.

FIGS. 8A–G illustrate one embodiment of a slider of the device of FIGS. 5A–C.

DETAILED DESCRIPTION OF THE PREFERRED EMBODIMENT

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

The fixation plate described herein differs from existing plates by allowing compression of the graft, and fixation of the plate in the vertebral bodies. Compression of the graft will improve fixation and reduce failure rates. According to Wolff's law, bone that is under compression will fuse. Currently, plates are placed without compression. This practice may create a permanent distraction component, which could ultimately result in failure for osteointegration. On the other hand, the compressible plates described herein allow compliance with Wolff's law, thereby significantly improving the chances of successful fusion. Thus, the compressible fixation plate described herein offers important advantages over present-day plate fixation. These plates are especially useful for cervical spinal surgery, but can be used on all portions of the spine with appropriate sizing.

Figure 1:
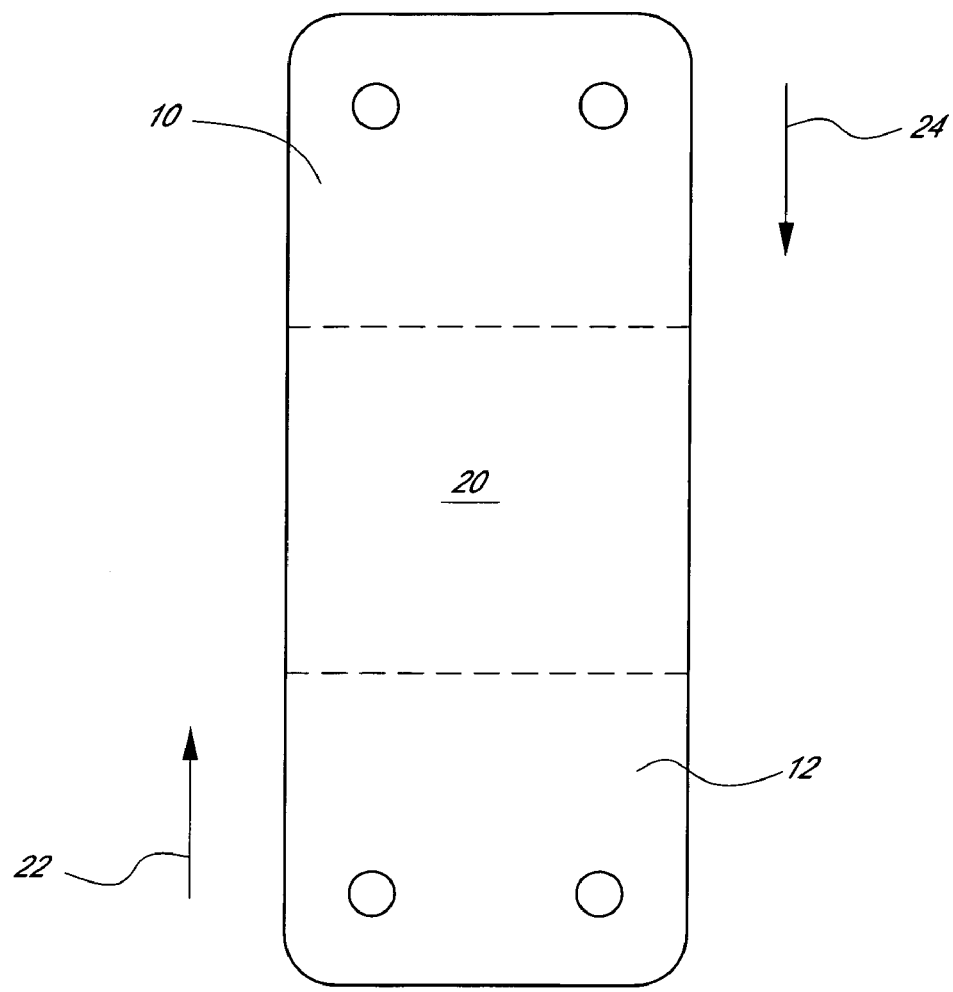
FIG. 1 is an illustration of a compressible spinal fixation device according to one embodiment of the invention.

One embodiment of a compressible spinal fixation plate is illustrated in FIG. 1. As illustrated in this Figure, a spinal fixation apparatus in accordance with this embodiment includes superior and inferior endpieces 10, 12 which advantageously include some form of fixation structures such as screw holes for attachment to respective upper and lower vertebral bodies. Located intermediate to the endpieces is a compressible portion 20. In operation, the endpieces may be affixed to respective upper and lower vertebral bodies, with one or more disk spaces positioned in between. After installation, the compressible portion 20 is compressed such that the two endpieces are forced toward one another, compressing the intermediate disk spaces in the process. This in turn compresses any graft that has been placed within the disk space(s), and improves the fusion process.

Figure 2:
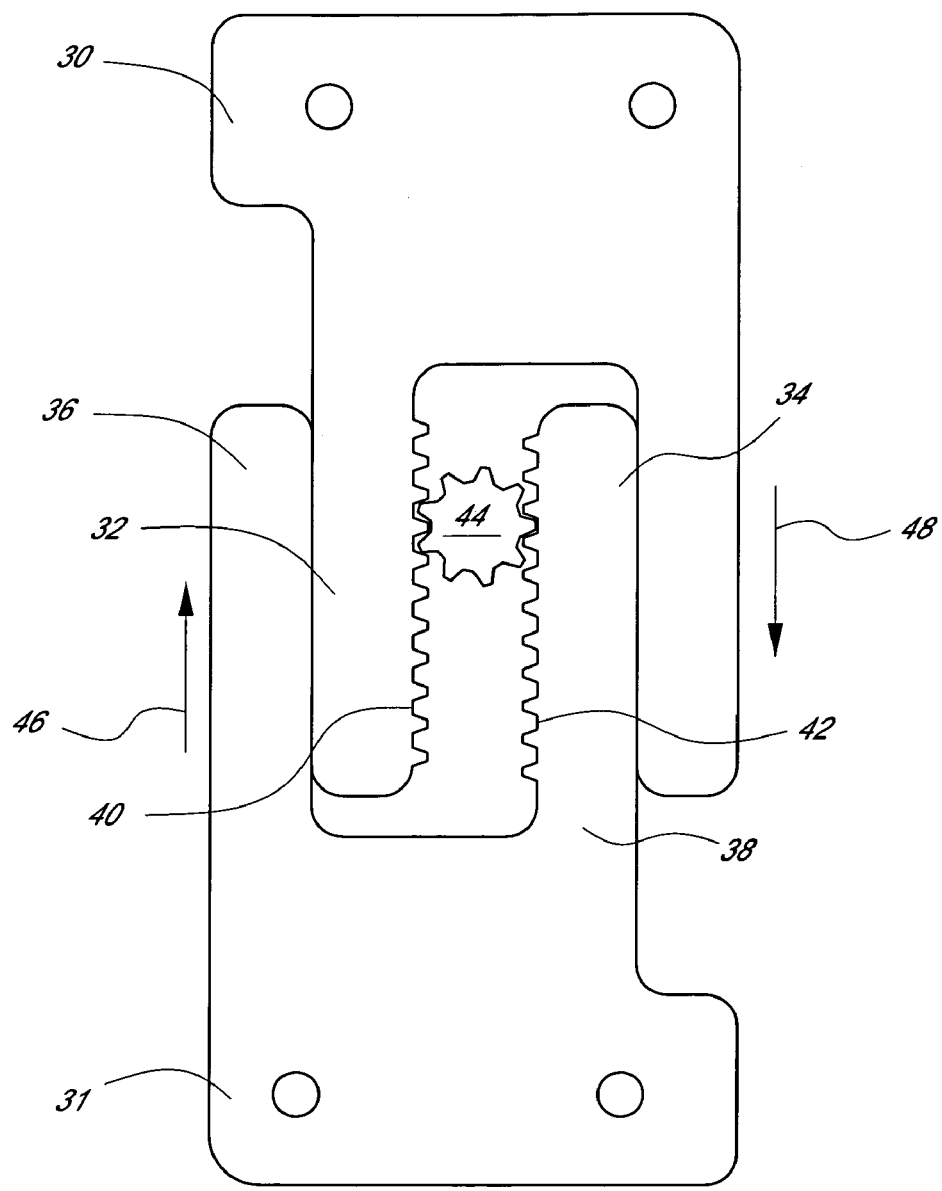
FIG. 2 is an illustration of a specific embodiment of a compressible portion of a spinal fixation device.

It will be appreciated that a variety of implementations of a compressible region 20 may be implemented. FIG. 2 illustrates a spinal fixation device that incorporates a specific embodiment of the compressible region 20 of FIG. 1. In this embodiment, the upper endpiece 30 includes a pair of arms 32, 34, to form a generally U-shaped body. The lower endpiece 31 also includes a pair of arms 36, 38 to form a generally U-shaped body. The respective arm pairs face each other and mate in a slidable fashion forming a structure with a pair of outer arms 34, 36 which surround and slide along a pair of inner arms 32, 38.

The inwardly directed faces of the inner arms 32, 38 include teeth 40, 42 respectively. These teeth mate with the teeth of a central gear 44. Thus, when the gear 44 is rotated counter-clockwise, the endpieces 30, 31 are drawn toward each other in the direction of arrows 46, 48. This reduces the overall length of the device by compressing this middle region of the apparatus, and accordingly compresses any intermediate disk space as described above.

Figure 3:
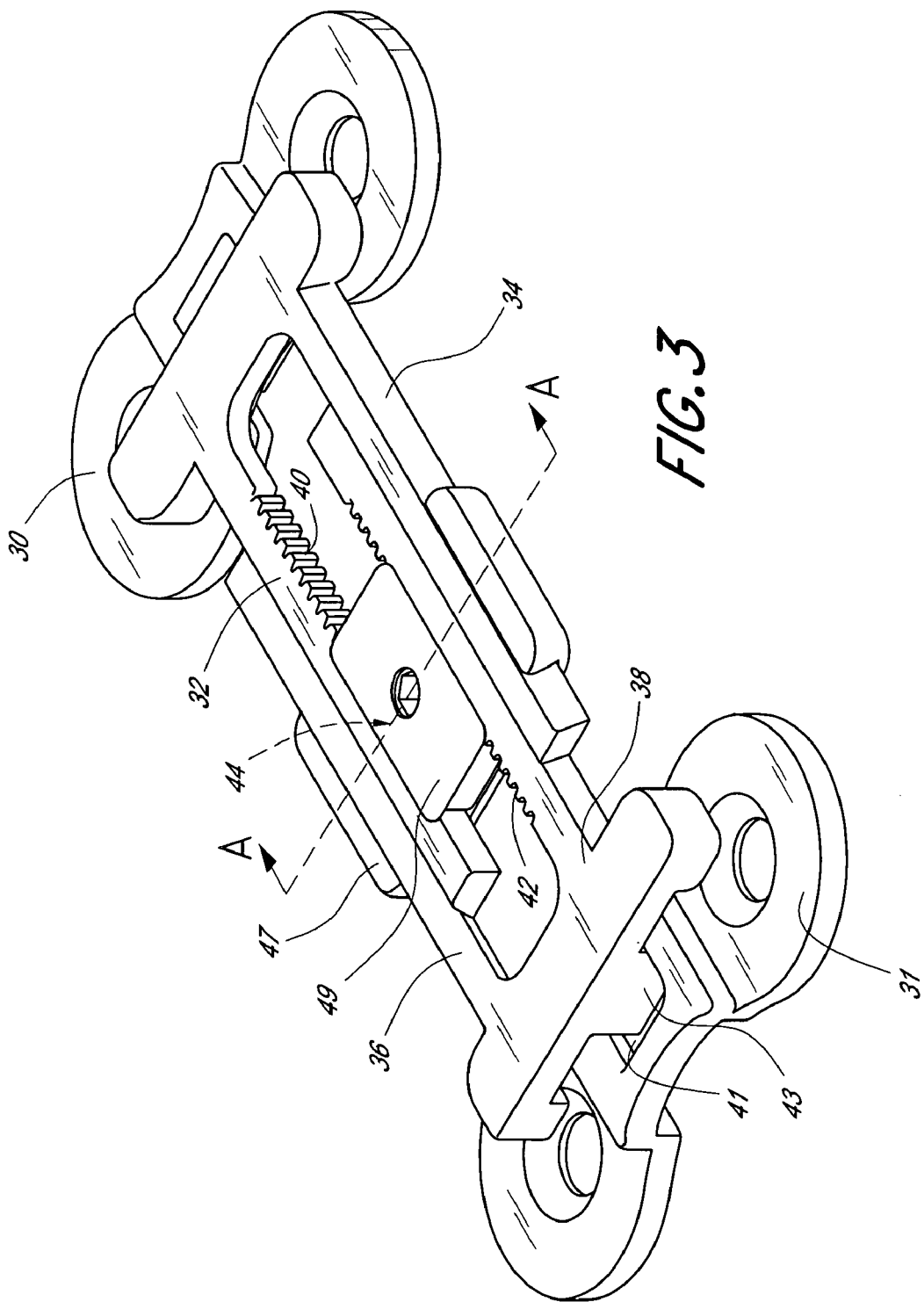
FIG. 3 is an illustration of another embodiment of a compressible fixation device.

FIG. 3 illustrates an embodiment similar to that shown in FIG. 2. In this embodiment, the gear 44 is captured within a two piece housing 47, 49 that captures the arms and gear in the central region of the device. The housings can be held together with screws from the rear, for example. In some embodiments, a hole for a set screw (not shown, but see also FIG. 5) is placed through the housing pieces 47, 49, such that when the set screw is installed, the gear is prevented from rotating, thereby locking the device in the compressed position after the gear is rotated to set the overall compressed device length after installation.

FIG. 3 also illustrates an alternative configuration for the attachment of the arm segments 32, 34, 36, 38 to the endpieces 30, 31. In the embodiment of FIG. 2, the endpieces are integral with the arm segments. In the embodiment of FIG. 3, however, the endpieces 30, 31 contain an opening 41 which engages a hooked flange 43 provided as part of a separate slider piece that incorporates the arm segments. With this design, the endpieces can be attached to their respective vertebral bodies first, and the central commpressible region can be attached to them after endpiece installation. It will be appreciated that other boding mechanisms between endpieces and slider pieces may be provided such as screws, rivets, etc.

For multi-level fusions, the device in FIG. 3 can be modified such that the lower housing portion 47 includes flanges and ports for bone screws such that the housing portion 47 can be affixed to an intermediate vertebral body. Multi-level fusions can also be accommodated by hooking a second slider piece into one of the openings 41 in one of the end pieces. This would then engage with another slider above or below such that three endpieces (an upper, lower and intermediate) are joined by a pair of adjacent compressible segments. In this case, the intermediate endpiece would have two sliders engaged in its central opening 41. Alternatively, separate fixing plates may be attached to the slider arms themselves.

Figure 4:
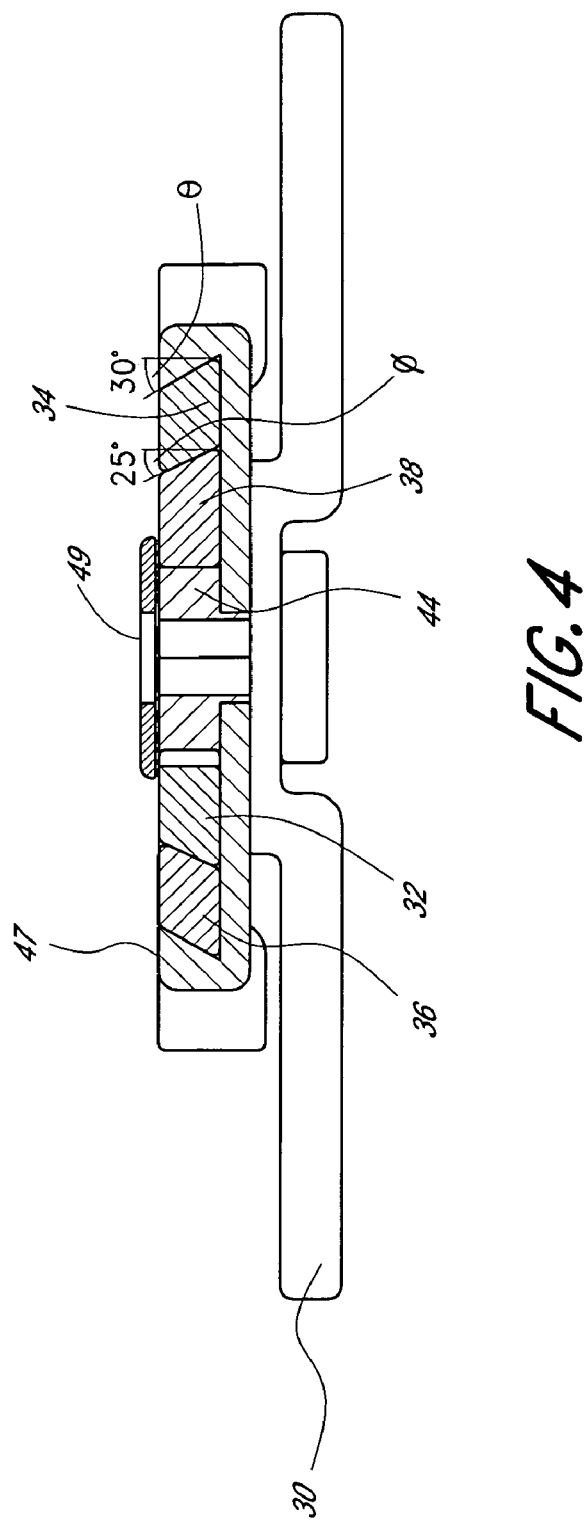
FIG. 4 is a cross sectional view along line A—A of the device of FIG. 3.

FIG. 4 is a cross section along line A—A of the device shown in FIG. 3. In this embodiment, the sides of the arm segments are angled or beveled to provide a mating surface that resists relative vertical displacement of the arms with respect to one another. In some advantageous embodiments, the bevel angle (θ) of the arm segments where they contact the housing 47 is different from the bevel angle (φ) of the arm segments where they contact each other. This facilitates capture of the arms within the housing and to each other. In one specific embodiment the angle θ is about 30 degrees and the angle φ is about 25 degrees.

Figure 5A:
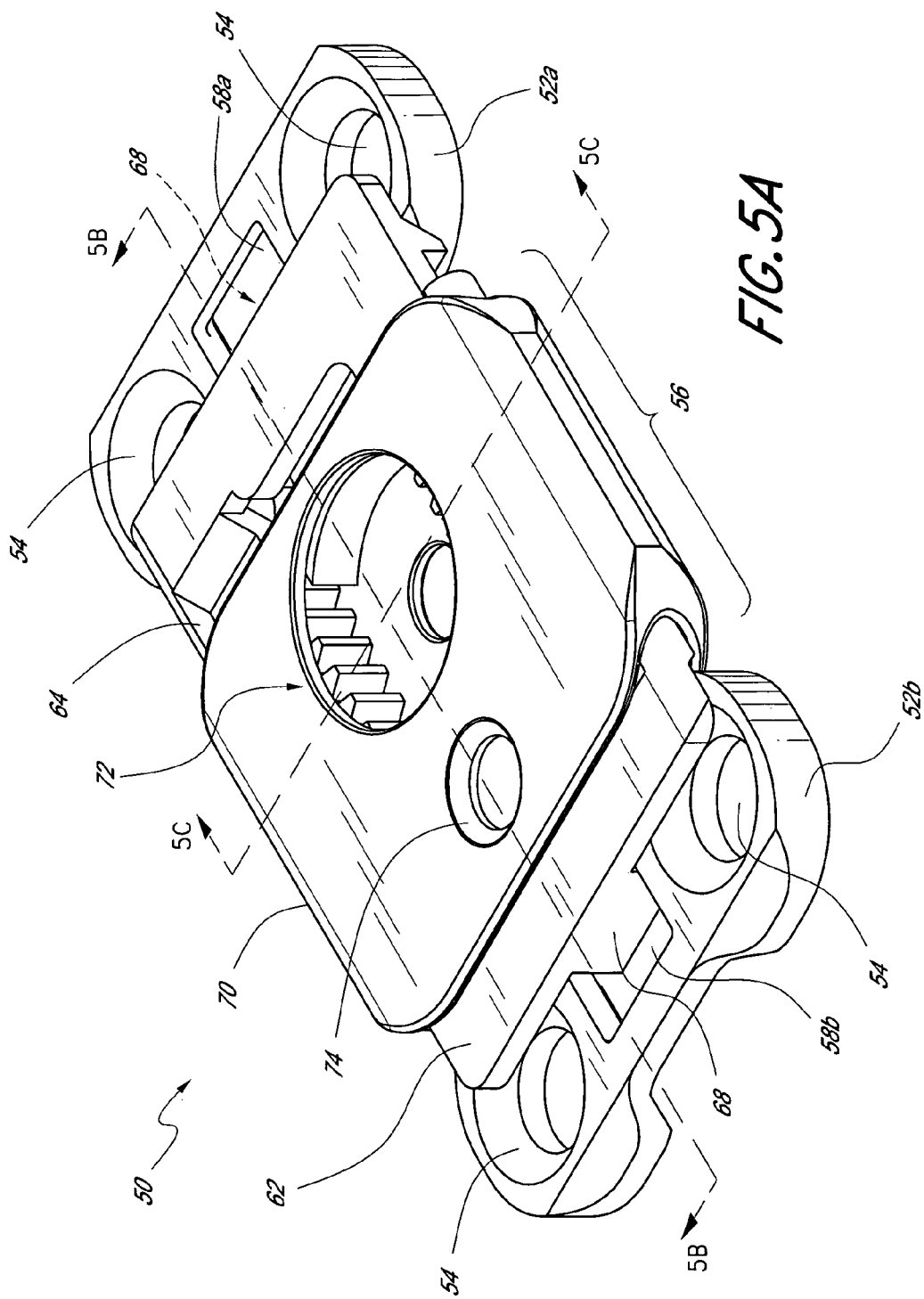
FIG. 5A is a perspective illustration of one embodiment of a compressible spinal fixation device.

A more detailed illustration of one specific embodiment of a compressible plate 50 is illustrated in FIG. 5A. In this embodiment, the apparatus 50 comprises two endpieces 52A–B, wherein each endpiece 52A–B is configured for attachment to a vertebral body with bone screws, for example, via a plurality of apertures 54. Ports 58A–B in the endpieces 52A–B link the endpieces 52A–B to a sliding compression mechanism 56, wherein the sliding mechanism 56 is designed to compress the vertebral bodies to which the endpieces 52A–B are attached.

The sliding compression mechanism 56 comprises a first slider 62 and a second slider 64 each having an approximately U-shaped geometry, wherein at least one arm of each slider 62, 64 has a plurality of teeth 66 for engaging a gear (not shown). In the embodiment shown, each slider 62, 64 has a flange 68 configured to engage the port 58A–B on the endpiece 52A–B. In an alternative embodiment, the sliders may be integral to the endpieces. The arms of the slider pieces 62, 64 are configured to slide over each other within the housing 70. Shown are first and second sliders 62, 64 designed so that each slider has a toothed arm and a non-toothed arm, wherein the toothed and non-toothed arms are parallel to each other. In the embodiment shown, the first and second sliders 62, 64, are configured such that the toothed arm of first slider 62 slides over the non-toothed arm of second slider 64, and the toothed arm of the second slider 64 slides over the non-toothed arm of first slider piece 62.

In the embodiment shown in FIG. 5A, housing 70 comprises a gear hole 72 for operation of the sliding mechanism 56. Before or after installing the device, a gear is inserted into hole 72 so as to engage the teeth 66 of each slider piece. The gear is rotated with a tool, causing the slider arms to move relative to one another, thereby pulling the endpieces 52A–B towards each other, and compressing the bone graft. A hole 74 for a set screw is also provided in this embodiment. When tightened, the set screw clamps the housing over the mated arms of the sliders 62, 64, securing the device in the compressed position. In this embodiment, the gear can be removed and the apparatus will remain fixed in the compressed position. In either this or the embodiments previously described, a ratcheting mechanism may also be installed in conjunction with the gear. In this embodiment, as gear turning engages the ratchet, the device will stay in the compressed position such that prior to installing the set screw, or if the surgeon wants to loosen the set screw, the device won't expand back to an elongated position.

Figure 5B:
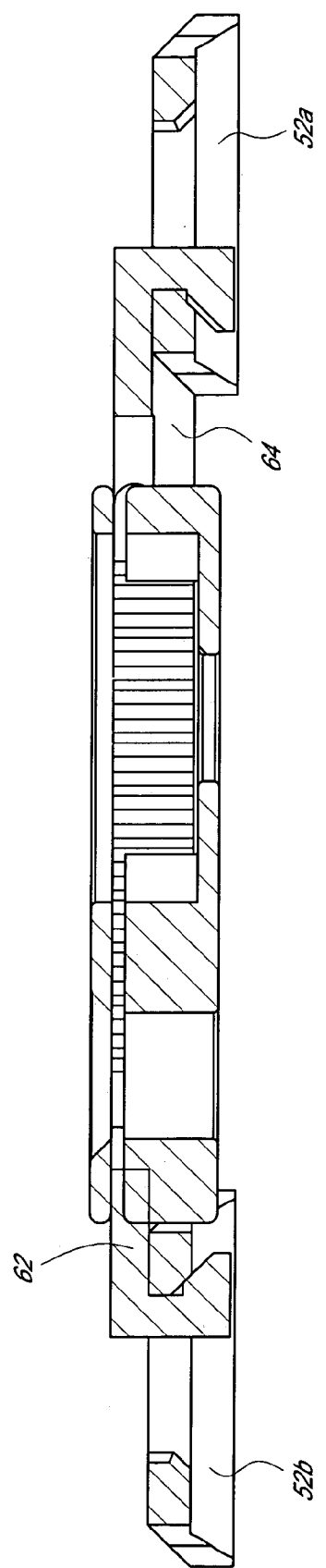
FIG. 5B is a cross-sectional view of the compressible device of FIG. 1A, taken along line A—A of FIG. 5A.

FIG. 5B is a cross-sectional view of cervical plate 50 taken along line A—A of FIG. 5A. In this embodiment the sliders 62, 64 each has flange 68 at one end of the parallel arms. Flanges 68 extend through ports 58A–B of endpieces 54A–B. The arms of sliders 62, 64 are shown with lips that extend around the bottom face of apertures 58A–B. This design facilitates attachment of the whole compression mechanism 56 to endpieces 52A–B. Housing 70 is shown with gear hole 72 providing an opening through housing 70 to expose the teeth 66 of the slider piece, making teeth 66 available for engagement with a gear (not shown).

FIG. 5C is a cross-sectional view of cervical plate 50 taken along line B—B of FIG. 5A. Toothed arm of first slider 62 is shown extended over non-toothed arm of second slider 64. The teeth 66 of first slider are exposed in gear hole 72. Parallel to the toothed arm of first slider piece 62 is shown the toothed arm of second slider piece 64. The toothed and non-toothed arms fit together in approximately the same shape of two L's wherein the long ends of each L rest against each other, and horizontally within housing 70. The shorter ends of each L are parallel to each other and are on opposite sides of the long ends of each L. The shorter ends comprise the outer edge of the non-toothed arm, and the inner, toothed-edge of the toothed arm of the mating arms. The inner edge of each slider comprises teeth 66. Teeth 66 face inwards towards the other arm of the same slider piece, and are exposed in gear hole 72. The outer edge of each slider runs along the inside wall of housing 70.

Figure 6C:
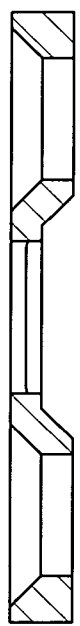
FIGS. 6A–D illustrate one embodiment of the endpiece of the device of FIGS. 5A–C.
Figure 6D:
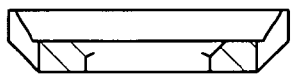
Figure 6A:
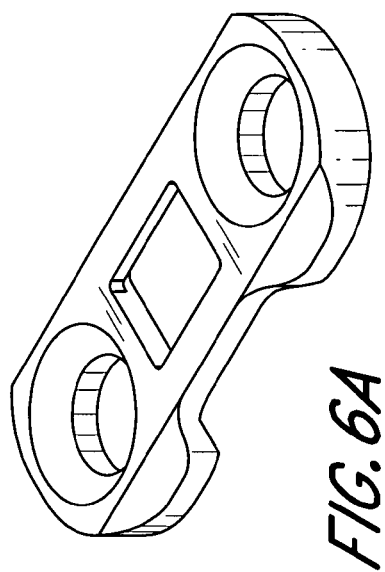
Figure 6B:
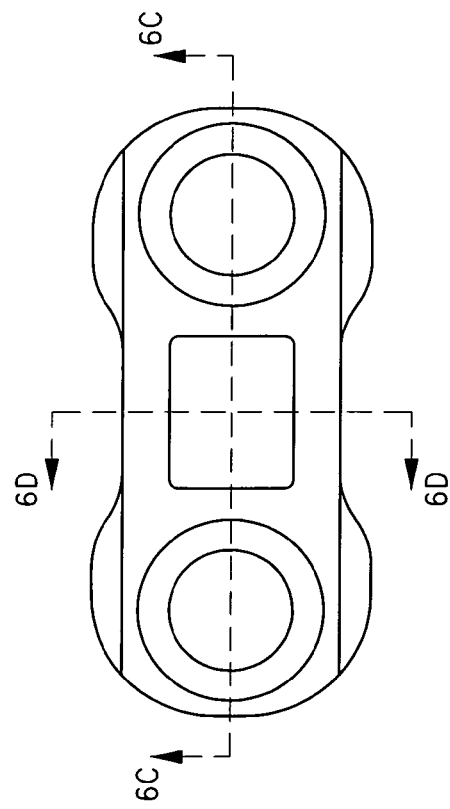

FIGS. 6A–6D, illustrate in more detail the endpieces 52A–B. FIG. 6A is a perspective view of the end plate 52, showing apertures 54, and port 58. As shown in FIG. 6B, endpieces 52A–B may be contoured around apertures 54. FIG. 6C is a cross section of FIG. 6B taken along line A—A. In this embodiment the top face round apertures 54 slope down towards the center of the circle, providing a convenient mechanism to house the head of a bone screw (not shown). FIG. 6D is a cross section of FIG. 6B taken along line B—B. This drawing further illustrates the angle of the top face of apertures 54 designed to accommodate the head of the fastening device.

FIGS. 7A–7D illustrate in more detail the housing 70 of the embodiment shown in FIG. 5A. 7A is a perspective view of housing 70. Hollows extend along parallel to each other through housing 70. Each hollow is configured to accommodate a pair of mating arms of first and second sliders 62, 64. Separating the two hollows is lock mechanism, such as a set crew mounting hole, 74 and gear hole 72. Apart from the hollows to accommodate the arms of sliders 62, 64, the aperture 74 configured to house a lock, and gear hole 72, the housing may be one integral solid part. The top face of housing 70 slopes inwards around the opening of lock mechanism 74, providing a convenient mechanism to house a locking device, such as a screw (not shown).

FIG. 7B is a top plan view of housing 70. As seen in this figure, the opening in the top face of housing 70 comprising the top face gear hole 72 is larger than the opening in the bottom face of housing 70 comprising the bottom face of gear hole 72. FIG. 7C is a cross-sectional view of FIG. 7B, taken along line A—A, along the diameter of gear hole 74. FIG. 7C shows the openings in the top face and bottom face of housing 70 comprising gear hole 72. FIG. 7D is a cross-sectional view of housing 70 taken along line B—B.

FIGS. 8A–8D illustrate in more detail one of the slider pieces 62, 64. FIG. 8A is a perspective view of first slider piece 62. Shown is the approximate U-shape of slider piece, 62, comprising parallel toothed and non-toothed arms. Both arms are perpendicular to a back that comprises flange 68 to facilitate attachment to the port 58A of endpiece 54. When first and second sliders 62, 64 are assembled together to form sliding compression mechanism 56, each set of mating arms fits within a hollow of housing 70.

FIG. 8B is a top plan view of a sliders 62, 64. In this embodiment, the toothed arms of sliders 62, 64 are configured to accommodate the non-toothed arm of the mating slider underneath the toothed arm. The non-toothed arms of sliders.

FIG. 8C is a cross-sectional view of FIG. 8B along line A—A. This view depicts the arrangement of a toothed arm of first slider 62 mated with a non-toothed arm of second slider piece 64. Shown is the arrangement of the arms of sliders 62, 64, described above, wherein the arms fit together in approximately the shape of two L's fit together. In this configuration, the outer edge of the toothed arm does not contact the housing. Rather, the edge opposite the teeth of the toothed arm runs along an edge of the non-toothed arm of second slider piece 64.

Figure 8G:
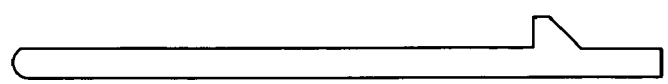
Figure 8F:
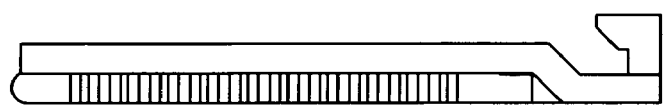
Figure 8E:
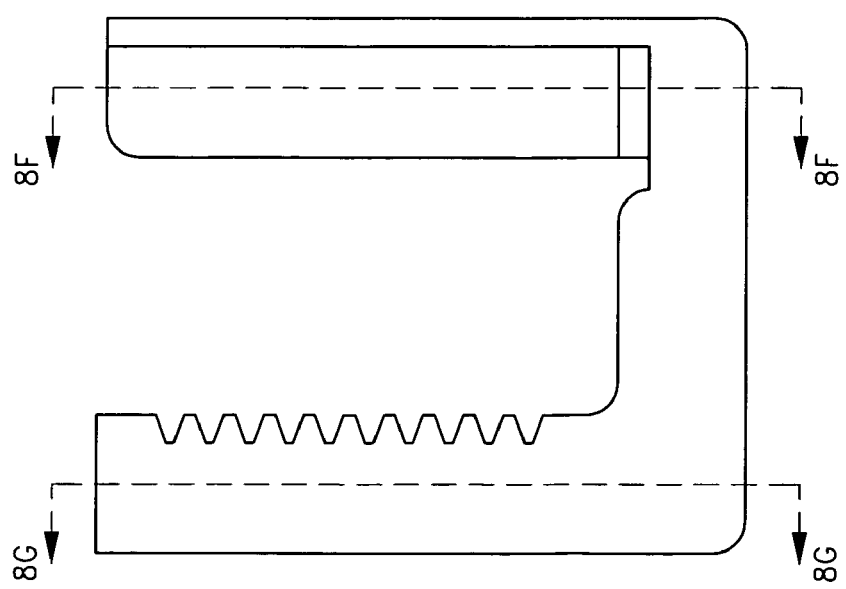

FIGS. 8E–8G illustrate in more detail an embodiment of first slider piece 62. FIG. 8E is the same view of first slider piece 62 as FIG. 8B. FIG. 8F is a cross-sectional view of FIG. 8E taken along line C—C. In the embodiment shown, the junction of the arms and the backs of each slider 62, 64 is angled. FIG. 8G is a cross-sectional view of FIG. 8E taken along line D—D. As depicted in FIG. 8G, the junction of the arms and the back of the slider is angled.

Figure 9:
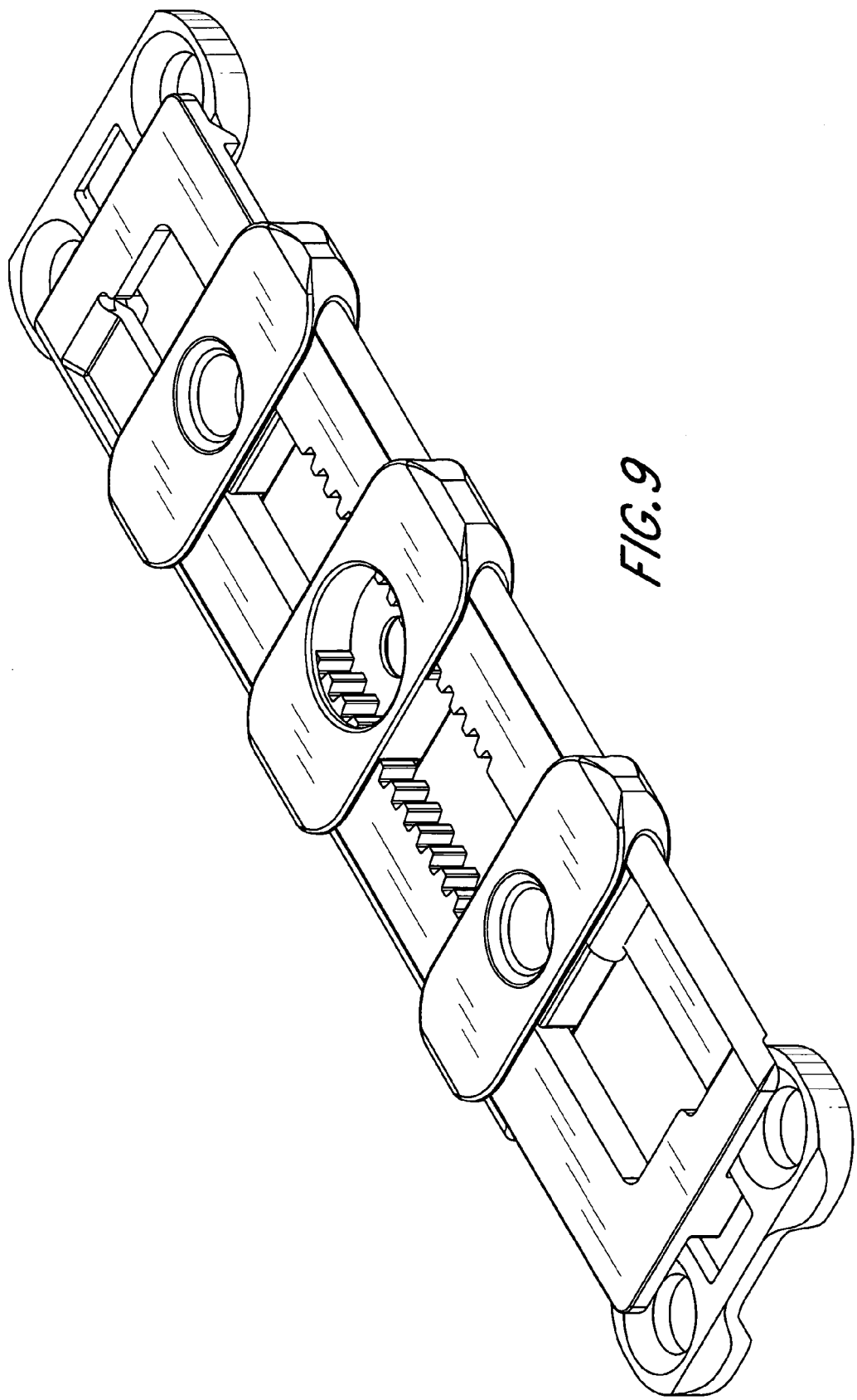
FIG. 9 is a perspective illustration of an additional embodiment of a compressible spinal fixation device.

An additional embodiment of a compressible plate is illustrated in FIG. 9, wherein a plurality of lock housings are provided which attach to the arms of the sliders 62, 64 intermediate the endpieces 52A, 52B. This device may also be advantageous in a multi-level application where a longer device is needed.

The traditional approach to the anterior cervical spine may be the same for the placement of the plate described herein when used in a cervical application. A transverse or oblique incision is made on the right or left side of the neck. The medial border of the sternocleidomastoid is retracted along with the carotid sheath. The trachea and the esophagus are retracted to the opposite side, providing surgical access down to the prevertebral fascia. Sweeping in a cephalad and caudal direction enables access to the anterior vertebral column. This allows identification of vertebral bodies and disk spaces, including the disk or vertebral body affected by the pathology. Use of interoperative x-rays at this stage confirms the location of the pathology. A surgeon then removes the affected disk(s) or vertebral body. If a diskectomy is performed, following removal of the disk, some of the cartilaginous end plate may be denuded to allow better incorporation of bone on bone surfaces in compression.

Those skilled in the art of orthopedic and neurosurgery can install the device described herein using standard surgical tools. The plate may, for example, be applied in a similar manner in the midline of the anterior cervical region spanning a distance of the graft. The present invention allows the surgeon to advantageously place the upper and cervical portions in the mid-substance of the vertebral bodies. By affixing the plate to the mid-substance of the vertebral bodies, the best purchase in the bone as well as avoidance of abutment between the plates and adjacent disks is achieved. This placement minimizes the possibility of adjacent segment disease or break out of the screws from the vertebral body and subsequent loosening of the graft. In short, placement of the screws in the upper and lower cervical vertebral bodies such that the graft is now capable of being compressed, provides the best possible construct for ensuring a cervical fusion. The capability of compressing the graft as well as anchoring in the best bone superior and inferior to the graft minimizes the risk for pseudarthrosis, graft migration, and/or screw dislodgment.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. An apparatus for the enhancement of fusion of at least two adjacent vertebrae comprising:
    at least a superior and an inferior endpiece, wherein said superior endpiece is adapted to be affixed to a superior vertebral body, and said inferior endpiece is adapted to be affixed to an inferior vertebral body; and
    a compressible sliding section, wherein said sliding section comprises a first slider and a second slider, and wherein each back of each slider comprises a flange that fits within a port in each endpiece, thereby joining each slider to a respective endpiece.

2. The apparatus of claim 1, wherein said sliding section comprises:
    a first slider and a second slider, wherein said first and second slider have approximately U-shaped geometry, and each slider further comprises:
    a first arm,
    a second arm, and
    a back, wherein said first arm and said second arm of each slider are parallel, wherein said first arm of said first slider mates with said second arm of said second slider, and said second arm of said first slider mates with said first arm of said second slider, such that said backs of said sliders are positioned parallel to each other, wherein each back of each slider comprises a flange that fits within a port in each endpiece, thereby joining the slider and endpiece,
    a plurality of teeth located on at least one of said first arms, wherein said teeth face towards said second arm of the same slider piece,
    a gear engaged with said plurality of teeth, wherein rotating said gear moves the arms within each set of mating arms relative to each other, positioning the apparatus into a compressed arrangement.

3. The apparatus of claim 2, further comprising a housing, wherein said housing further accommodates said sliders and said gear.

4. The apparatus of claim 2, further comprising a lock to secure the apparatus in a compressed configuration.

5. The apparatus of claim 2, wherein each back of each slider is integral to an endpiece, thereby joining the slider and endpiece.

6. The apparatus of claim 2, further comprising a fixing plate, wherein said fixing plate is located between said superior and said inferior endpieces and is positioned and configured to be affixed to an intermediate vertebral body located between said superior and said inferior vertebral bodies.

7. The apparatus of claim 6, wherein the fixing plate is located between and connected to said mating arms of said slider pieces.

8. The apparatus of claim 1, wherein the plate is contoured to accommodate lordosis.

9. The apparatus of claim 1, wherein the apparatus is made of a bioabsorbable material.

10. The apparatus of claim 1, further comprising: at least one intermediate endpiece, wherein each said intermediate endpiece is located between two endpieces, wherein one endpiece is superior to and the other endpiece is inferior to said intermediate endpiece, and wherein said intermediate endpiece is adapted to be affixed to a vertebral body intermediate said superior and said inferior vertebral bodies, and wherein said intermediate endpiece is connected to each said adjacent endpieces via a compressible device.

11. A method of enhancing fusion between vertebral bodies comprising:
    accessing a spinal portion;
    affixing respective endpieces to superior and inferior vertebral bodies;
    engaging a compressible central body with said endpieces after said affixing by fitting a flange on the back of a slider to a port in at least one of said endpieces;
    adjusting the distance between said endpieces into a compressed position; and
    locking said apparatus in the compressed position.

12. The method of claim 11, wherein adjusting the distance between said endpieces further comprises sliding each mate in a set of mating arms relative to each other.

13. The method of claim 12, wherein sliding each mate in a set of mating arms relative to each other further comprises turning a gear engaged to a plurality of teeth on at least one arm within at least one set of mating arms.

14. A method of enhancing fusion in a multilevel vertebral fusion comprising:
    accessing a spinal portion;
    removing some or all of at least two spinal disks;
    affixing respective endpieces to superior and inferior vertebral bodies;
    affixing at least one intermediate endpiece to an intermediate vertebral body between said superior and inferior vertebral bodies;
    engaging a compressible central body with said intermediate endpiece and another one of said endpieces after said affixing by fitting a flange on the back of a slider to a port in at least one of said endpieces;
    adjusting the distance between said engaged endpieces into a compressed position; and
    locking said engaged endpieces in the compressed position.

* * * * *